(12) United States Patent  (10) Patent No.: US 8,734,323 B2
Staffolani  (45) Date of Patent: May 27, 2014

(54) DEVICE FOR CARRYING OUT A SEXUAL ACT

(76) Inventor: Nicola Staffolani, Perugia (IT)

( * ) Notice: Subject to any disclaimer, the term of this patent is extended or adjusted under 35 U.S.C. 154(b) by 696 days.

(21) Appl. No.: 12/922,248

(22) PCT Filed: Mar. 17, 2008

(86) PCT No.: PCT/IT2008/000173
§ 371 (c)(1),
(2), (4) Date: Oct. 20, 2010

(87) PCT Pub. No.: WO2009/116092
PCT Pub. Date: Sep. 24, 2009

(65) Prior Publication Data
US 2011/0054251 A1   Mar. 3, 2011

(51) Int. Cl.
*A61F 5/00* (2006.01)
(52) U.S. Cl.
USPC ............................................. 600/39; 622/41

(58) Field of Classification Search
USPC ...................................................... 600/38–41
See application file for complete search history.

(56) References Cited

U.S. PATENT DOCUMENTS

| 4,407,275 | A | 10/1983 | Schroeder |
| 5,823,939 | A | 10/1998 | Tsagarakis |
| 6,193,753 | B1 | 2/2001 | Nordheim et al. |
| 6,659,938 | B1 | 12/2003 | Orlowski et al. |
| 7,527,589 | B2 * | 5/2009 | Squicciarini .................... 600/39 |
| 2003/0136415 | A1 | 7/2003 | Lanton, Jr. |

FOREIGN PATENT DOCUMENTS

DE         260938       6/1913

* cited by examiner

*Primary Examiner* — John Lacyk
(74) *Attorney, Agent, or Firm* — Lucas & Mercanti, LLP

(57) ABSTRACT

Device for fulfilling sex act comprising a prosthesis placed, at least partially, around the male-member, at the base thereof, characterized by comprising means for retaining in place said prosthesis around the member, and in that said prosthesis is inflatable.

14 Claims, 6 Drawing Sheets

DEVICE FOR CARRYING OUT A SEXUAL ACT

CROSS-REFERENCE TO RELATED APPLICATION

This application is a 371 of PCT/IT2008/000173 filed Mar. 17, 2008, the contents of which are incorporated herein by reference.

FIELD OF THE INVENTION

The present invention concerns to a device for fulfilling sex act. Particularly, such a device is adapted to be used by persons suffering of erectile malfunctions and then not being able to begin, or complete, a sex act with their own partner adequately.

BACKGROUND ART

Sex devices are known that are used to aid the fulfilling of sex act by persons who suffer of the afore mentioned malfunction.

Particularly, U.S. Pat. No. 4,488,541 describes a sex device comprising a prosthesis placed around the male member, at the base thereof, and means to retain said prosthesis in position around the member.

Also U.S. Pat. No. 1,216,099 and FR 2687063 describe a sex device similar to that described in the United States document, wherein the connection between the prosthesis and the retaining means is respectively realized by reciprocally engagement or by Velcro, instead of by realizing the prosthesis and the retaining means as a whole.

However such devices are not free of drawbacks. Indeed, apart from being definitely embarrassing for shape and dimensions, they are not handy too. Such a latter drawback rises from the fact that the user, in case wherein he would be able to reach an erection during the sex act, could not cast off the device without being forced to suspend the sex act itself. Such a suspension could be detrimental because it may reduce the user excitement, and thereby hold down his stimuli.

Object of the present invention is to realize a device for fulfilling the sex act that could be put on without particular problems of psychological nature, and used without interruption during the whole sex act also in case of a complete erection of the user member. One more object of the present invention is to realize a device for fulfilling the sex act that allows not only the man, but the women too, to fulfill the sex act in presence also of serious erectile malfunctions of the man.

SUMMARY OF THE INVENTION

These and other objects are reached by the device for fulfilling the sex act according to the first independent claim and the following dependent claims.

The device for fulfilling sex act according to the invention comprises a prosthesis placed, at least partially, around the male member, at the base thereof, characterized by comprising means for retaining in place said prosthesis around the member, and in that said prosthesis is inflatable. In practice the prosthesis, when inflated, is able to raise the male member not yet erect, because it is retained in position by the afore said retaining means, thereby allowing the woman penetration. Such a solution offers the advantage of operating the prosthesis during the whole sex act, or by inflating it, in case of a reduction of the member erection, or by reducing its pressure, in case of member erection; everything without having to take out the device and thereby to suspend the coitus sharply.

Furthermore the prosthesis has a tubular shape and extends for a length of said male member. In practice it takes a closed ring shape.

According to a second embodiment the prosthesis has essentially a C-shape, i.e. an open ring shape, and comprises an elastic strip placed as a bridge over the two C-ends to limit the opening of said prosthesis when if is placed around said member, or when said member is erected.

Always according to the invention, and according to each embodiments of the invention, said prosthesis comprises a first outer surface, made of a material essentially anelastic, being biocompatible, antiallergenic, and in case greased too, and a second inner surface, made of a material essentially anelastic having the same characteristic of the outer surface, and placed facing the surface of said male member. In addition between said first and second anelastic surface there may be comprised a plurality of stiffening radial diaphragms and for maintaining the distance between the two surfaces, essentially anelastic too.

Both embodiments comprise first means to inflate said prosthesis.

According to a third embodiment of the invention, the prosthesis having an open ring shape, comprises a pad essentially elastic, inflatable and constrained to said prosthesis at said second inner surface. In this case such said first inflating means may be adapted for the inflation of the pad too, otherwise they may comprise second means to inflate said elastic pad independently from the first inflating means.

Both first and second inflating means are of the fluid-type, preferably of water or air type, or other similar means.

According to a fourth embodiment of the invention also the closed ring prosthesis may be provided with an elastic pad placed on the second inner surface of the prosthesis itself.

According to a characteristic aspect of the invention, said retaining means comprise a harness placeable around the user waist, of the tight underpants type, for example. Then such an underpants is able to retain in position the prosthesis, when it is inflated. In such a way the member too, although not erected, can assume a raised position. The prosthesis may be, either integral with said retaining means, and in such a case may be worn also a lot of time before the sex act, or may be connected to said retaining means by removable connecting means, of the bayonet type connecting means, for example, or male/female connecting means, or interference connecting means, or Velcro connecting means, or adhesion connecting means, or something else similar. In this latter case the user may connect the prosthesis shortly before having a sex act only, such as a prophylactic.

To aid the prosthesis introduction, and not to obstruct the member movement during the sex act, this could present, at its free end, a tapered shape.

BRIEF DESCRIPTION OF THE DRAWINGS

For purposes of illustrations and not limitative, more preferred embodiments of the present invention will be provided with reference to the accompanying drawings, in which.

DETAILED DESCRIPTION OF SOME EMBODIMENTS OF THE PRESENT INVENTION

Figure 1:
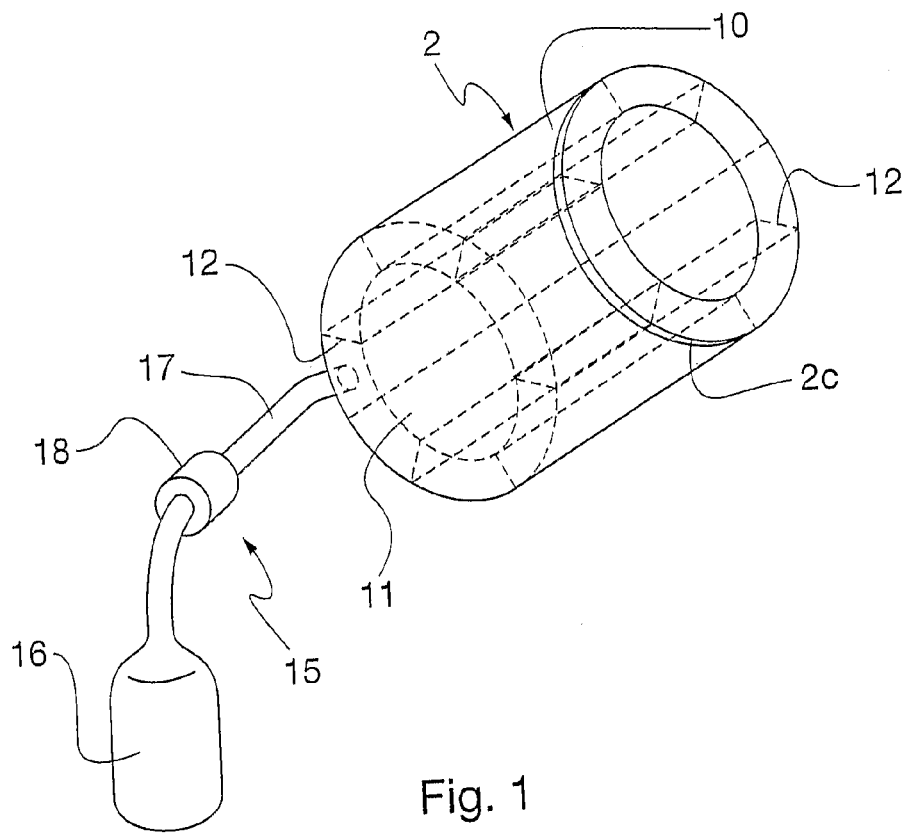
FIG. 1 is a prospective view of a prosthesis according to the invention.

Particularly referring to such a figure, a device 1 is indicated for fulfilling the sex act according to the present invention.

The device 1 comprises a prosthesis 2, inflatable, placed around the male member 100, at the base 104 thereof, and means 5 to retain the prosthesis 2, in position around the member 100. Such a solution offers the benefit of being able to inflate the prosthesis during the sex act, in case of reduction of the member erection, or on the contrary, to deflate the prosthesis 2 in case wherein the user has an erection during the sex act. Everything happens without having to take out the device 1 and thereby having to interrupt the coitus sharply.

Furthermore the prosthesis 2 has a tubular shape (FIG. 1) and extends for a length of said male member. In practice it takes a closed ring shape.

Figure 2:
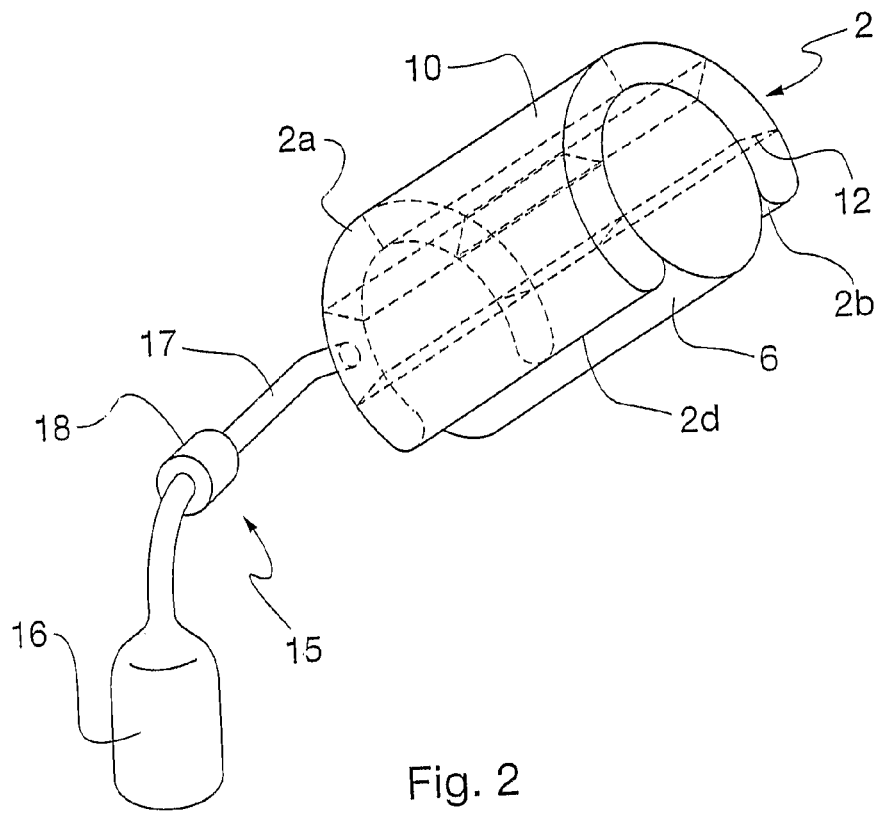
FIG. 2 is a prospective view of a prosthesis according to a second embodiment of the discovery.
Figure 3:
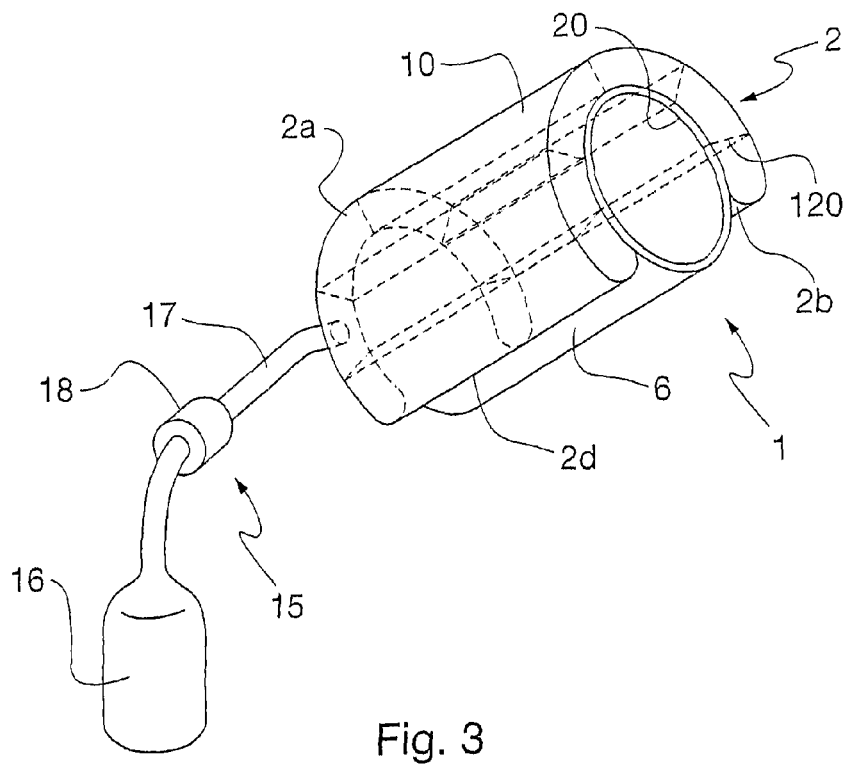
FIG. 3 is a prospective view of the prosthesis according to a third embodiment of the discovery.

According to a second embodiment (FIG. 2) of the invention, the prosthesis 2 has essentially, a C-shape, i.e. an open ring shape, and comprises an elastic strip 6 placed between the two C-ends 2d and 2b to limit the opening of said prosthesis 2 when it is placed around said member 100, or when said member is erected. Such an elastic strip has in addition the function of safety element in case wherein during the sex act, as consequence of inaccurate movements of his partner, there could be the risk of injuring or damaging the male member that is become integral to the prosthesis.

According to the invention too, and according to each of the embodiments of the invention, said prosthesis 2 comprises a first outer surface 10, realized by an essentially anelastic material, and a second inner surface 11, realized by an essentially anelastic material too, and placed facing the surface 101 of said male member 100. The chosen material for both the inner surface 10 and the outer surface 11 must be antiallergenic and biocompatible anyway. Furthermore between said first 10 and said second 11 anelastic surface may be comprised a plurality of stiffening radial diaphragms 120, essentially anelastic too, and having the task of limiting the prosthesis 2 dimension when inflated, and reducing the possibility of a possible prosthesis breaking when in use.

Each of the embodiments comprises first means 15 to inflate said prosthesis 2, which include a pressure reservoir 16 fluidically connected to the prosthesis by a first inlet duct 17. In practice, once the pressure reservoir is operated, at least part of the air, or other fluid, present in the reservoir, is transferred into the prosthesis, thereby enhancing the pressure, therefore inflating if. Furthermore the first inflating means 15 comprise a first valve system 18 disposed between the prosthesis 2 and the reservoir 16 and being able to regulate the prosthesis pressure. The first valve system 18 is indeed able both to maintain constant the pressure of the prosthesis 2, during the sexual act, and to allow the pressure reduction of the prosthesis 2, when desired by the user. Indeed it has to be observed that the valve system, in the afore mentioned case, may comprise a pressure reducer (not shown) able to allow the passage of the fluid sufficient only to reach the desired pressure, and a tap to reduce the pressure. Such inflating means 15 may be opportunely constrained to said retaining means 5 for the prosthesis 2 (FIGS. 5 to 9), so that one of the two ending parts of the first inlet duct 17 is placed at the prosthesis 2 base 2a, whereas the reservoir is placed on the top portion of the retaining means 5. However, although herein not shown, the first duct 17 may be also placed at the outer surface of the prosthesis, as well the reservoir may be placed in another position, without for this exiting from the scope of protection of the present invention. Alternatively such inflating means may comprise a second duct 17' and a second valve system 18' placed along said duct and allowing the deflating of the prosthesis in case, for example, when the user, after an erection, decides to reduce the pressure within the prosthesis. In this embodiment it is not necessary that the valve system 18, present along the duct 17, is able to reduce the inflating prosthesis pressure.

Furthermore such inflating means may comprise a bulb-shaped blower 16 operable by the user. In this case the duct 17 and the valve system 18 operate in the same manner above discussed.

According to a third embodiment of the invention, the prosthesis 2 having an open ring shape, comprises a pad 20 essentially elastic, inflatable and constrained to said prosthesis at said second inner surface 11. Such a second inner surface 11 may also be part of said pad 20, which will then be realized integral to the prosthesis 2 itself. In this case the prosthesis 2 may either adopt said first means 15 for inflating the pad 20 too, or comprise second means (herein not shown) to inflate said elastic pad 20, independently from the first inflating means 15. In every case, both first 15 and second inflating means are of the fluid-type, preferably of the water or air type or other similar means. The pad 20 presence has the function of retaining more efficiently the member 100 within the prosthesis 2, as well as regulating in the member the flow of venous and arterial blood during the whole sex act. Indeed, the alternate movement of the member during the women penetration, associated to the pad elasticity, are able to generate a peristaltic movement at the base 104 of the member 100 able to naturally regulate the venous and arterial pressure of the blood flowing in the male member.

Figure 4:
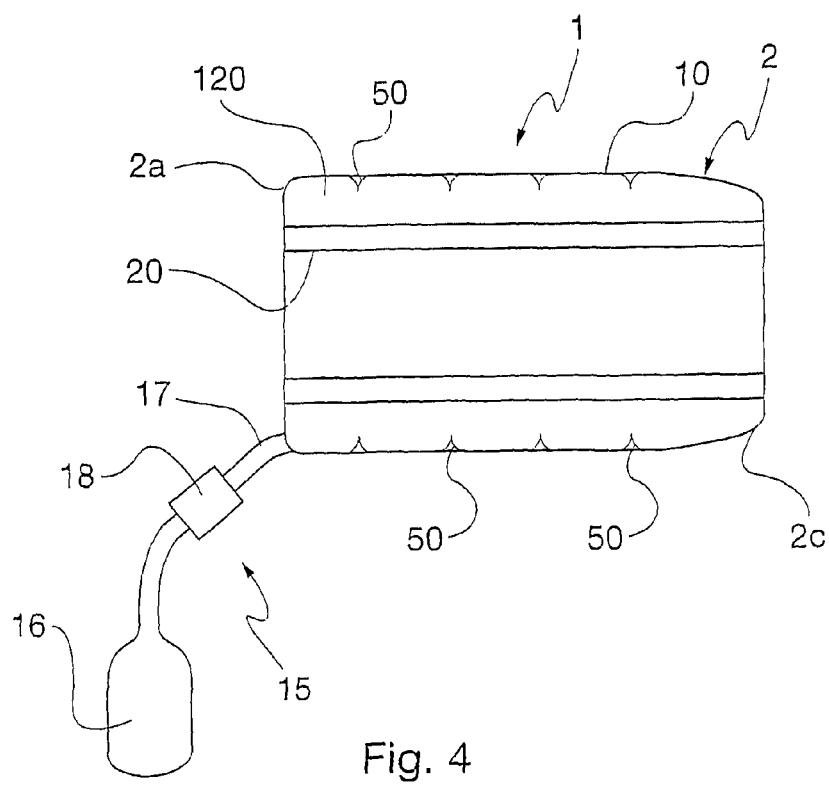
FIG. 4 is a longitudinal cross-sectional view of the prosthesis according to a fourth embodiment of the device.

According to a fourth embodiment of the device (FIG. 4) also the prosthesis 2, having the shape of a ring, comprises said inflatable pad 20 that may either be constrained to the second inner surface 11 of the prosthesis, or be partially made up of said second inner surface 11. According to a characteristic embodiment of the invention, said retaining means 5 comprise a harness 31 placeable around the user waist, of the underpants type, for example, that may advantageously be tight. Such an aspect may allow a better placement of the prosthesis 2 around the male member. Then such an underpants 31 are able to retain in position the prosthesis, when it is inflated. In such a way the member 100 too, although not erected, adopts a partially erected position, or anyway a raised position. The prosthesis 2 may be, either integral with said retaining means 31, or may be connected to said retaining means 31 by removable connecting means 32, of the type, for example, of bayonet connecting means (FIG. 9), or male/ female connecting means, or interference connecting means, or Velcro connecting means, or adhesion connecting means, or something else similar.

Figure 5:
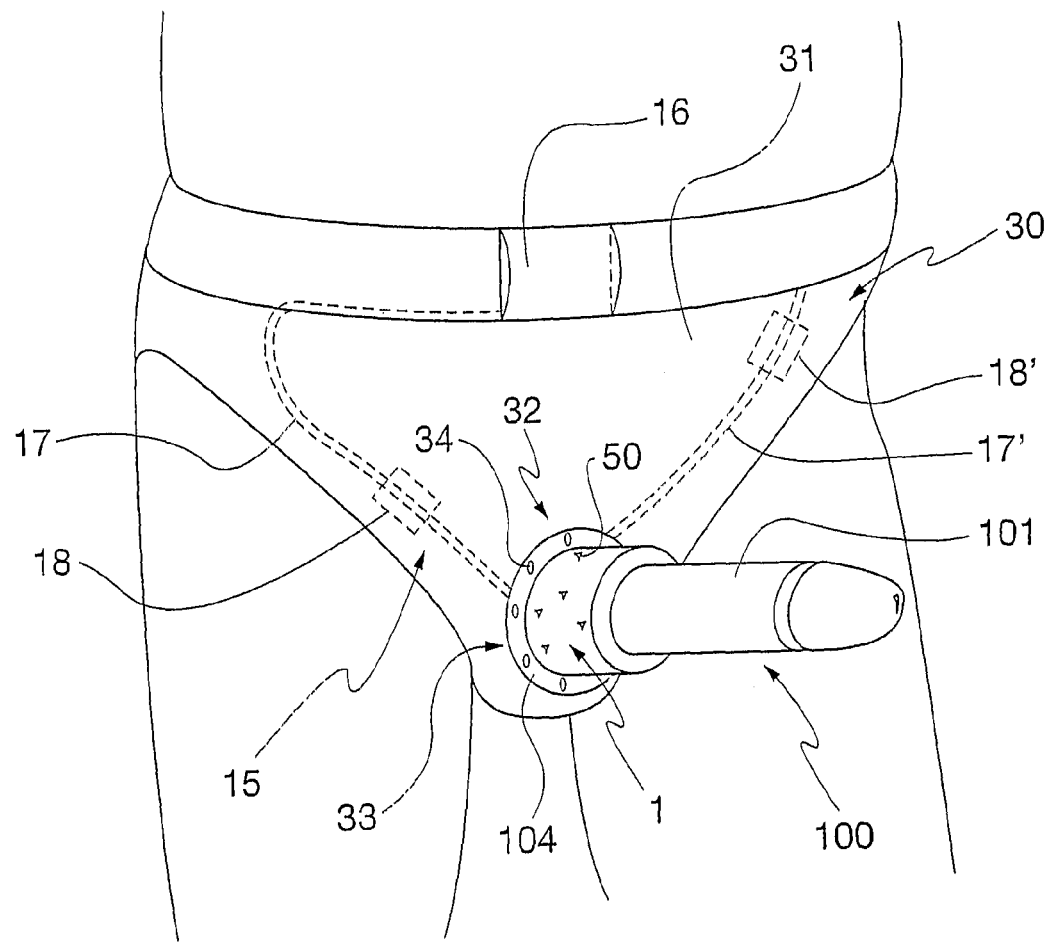
FIG. 5 is a prospective view of the device according to the invention applied around the user pelvis and provided with removable connecting means.
Figure 6:
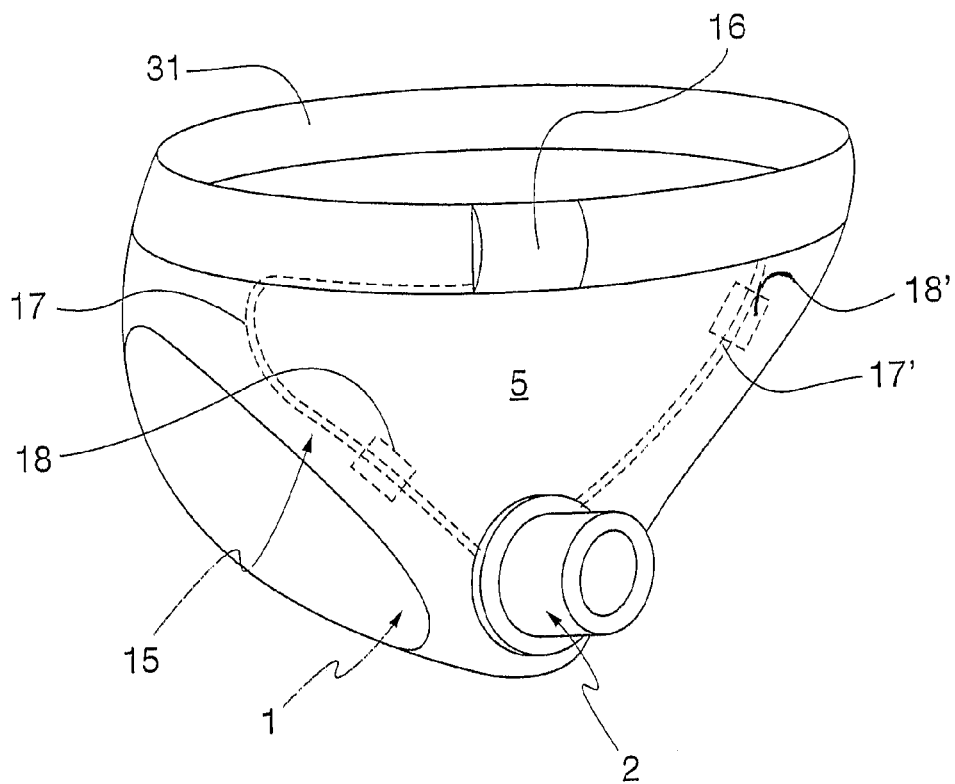
FIG. 6 is a prospective view of a device comprising retaining means integral with said prosthesis, after said prosthesis has been operated.
Figure 7:
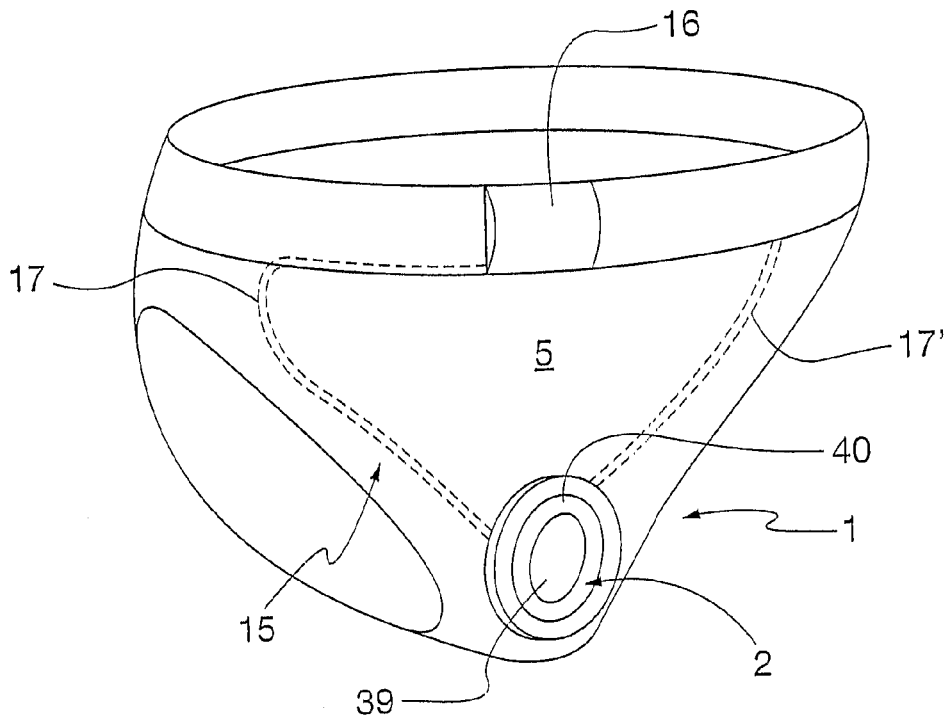
FIG. 7 is a prospective view of a device comprising retaining means integral with said prosthesis, before said prosthesis has been operated.
Figure 8:
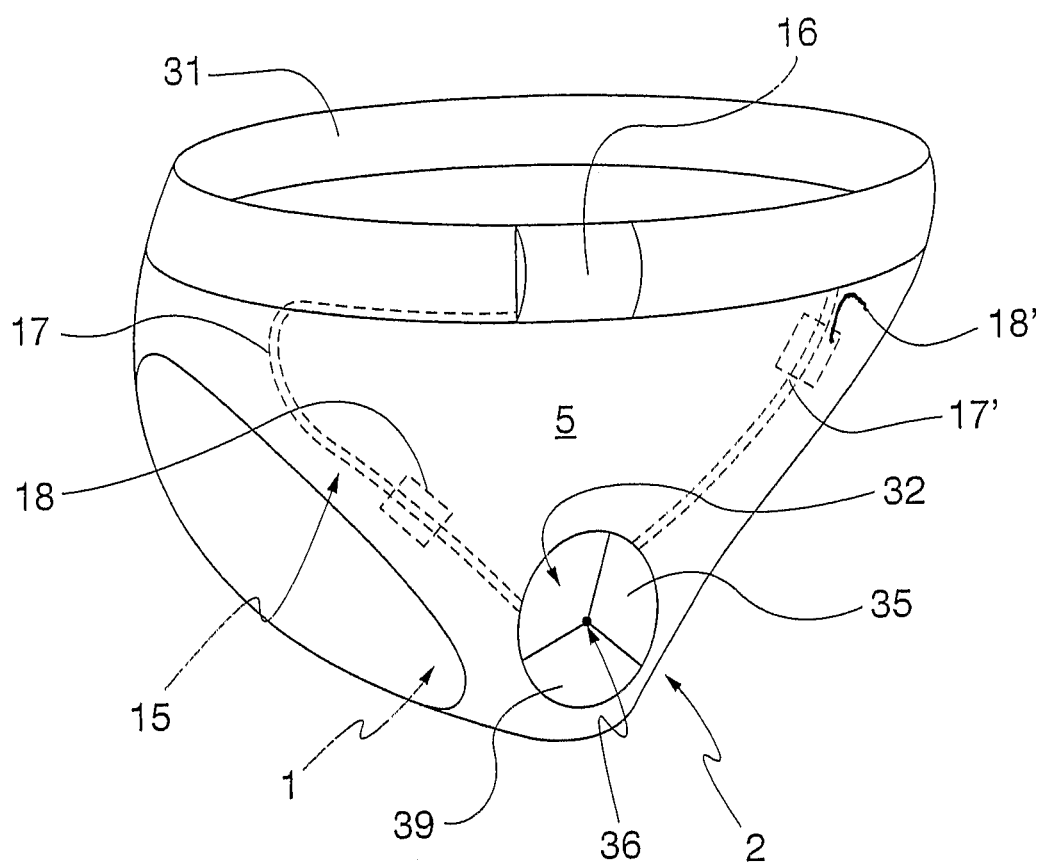
FIG. 8 is a prospective view of a device comprising retaining means provided with removable connecting means.

The removable connecting means 32 may comprise a flange 33 that can be connected to the underpants by elements of the button 34 type, for example, or other similar (FIG. 5).

According to a particular embodiment of the invention (FIG. 8), the connecting means 32 may be arranged at the opening 39 of the underpants 31 themselves. Such connecting means 32 may comprise three folding portions 35, realized with the same material of the underpants 31 and having a triangular shape, whose ending vertices coincide in a point 36 that is placed in the aperture 39 center. In such a way, the prosthesis 2 provided with a flange (not shown in figure) may be coupled to the underpants of the inner side thereof. This happens not before turning over the three portions over the inner side of the underpants, like valves, and having removed the protective film placed on the outer surface of the three portions, that covers completely an adhesive substance. So in practice, the flange of the prosthesis 2 rabbets against the peripheral edge of the opening 39, thereby coming in contact with the three folded portions, rendered adhesive by eliminating the surface film. The prosthesis thereby obtained is firmly retained by the three folded portions provided with an adhesive substance.

It has to be observed that the amount of folding portions 35 may also be different from three, without therefore exiting from the scope of protection of the present invention.

In case wherein the prosthesis 2 is integral with the underpants (FIGS. 6 and 7) it is possible to arrange around said opening 39, with an essentially circular shape, a suitable pocket 40 in which there is the prosthesis 2 completely folded. When necessary, the prosthesis 2 may be inflated, obviously not before removing a tongue (herein not shown), closing the pocket 40 and protecting the prosthesis before it would be used. Such a pocket 40 could be realized with a ring shape and could be arranged to cover the prosthesis 2 itself.

Furthermore, according to the embodiments herein described too, the prosthesis 2 may have a free end 2c having a slightly tapered shape (FIG. 4) such to aid the women penetration when the male member is not erected yet and the prosthesis 2 is inflated.

It has to be observed that along the outer surface 10 of the prosthesis 2 if is possible to arrange the depressed portions 50 filled with a wetting substance, for example, Vaseline, so that when the prosthesis 2 is inflated such depressed portions 50 are opened releasing such a wetting liquid.

It has to be further mentioned that the inflating pressure of the prosthesis, provided or not with a pad 20, may change according to the user and his partner sensations.

Figure 9:
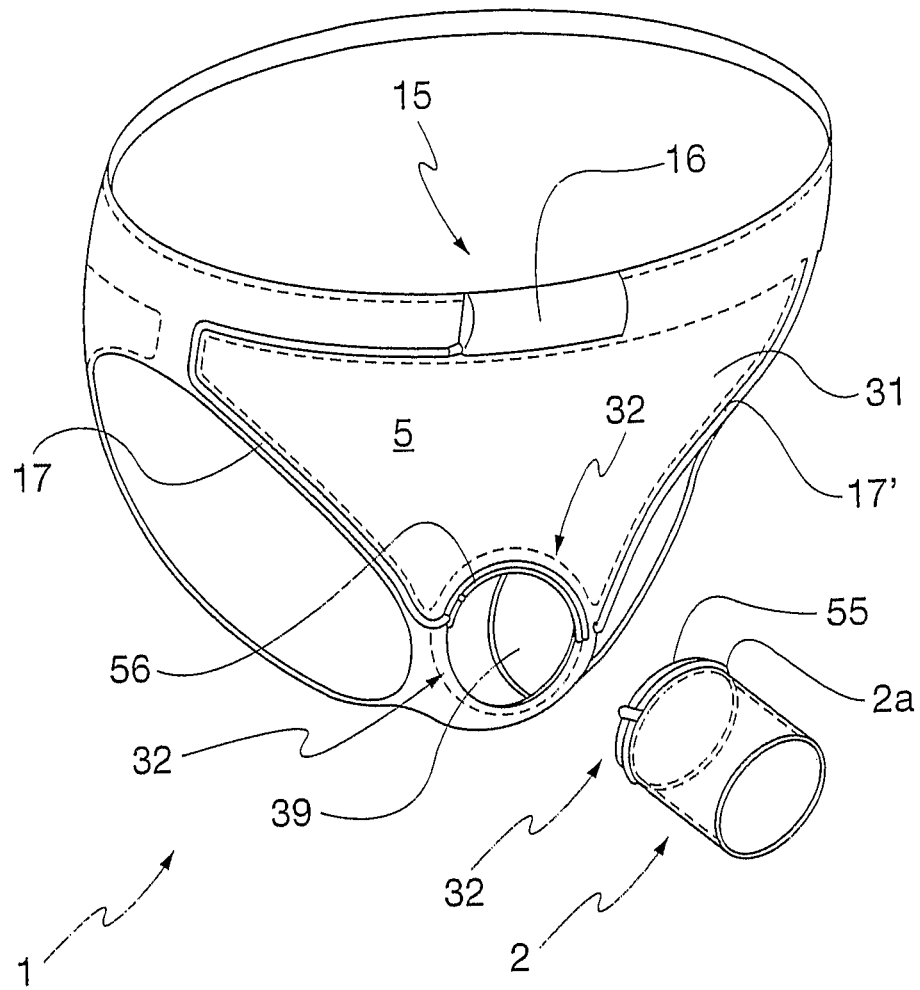
FIG. 9 is a prospective view of a device comprising retaining means provided with removable connecting means of the bayonet type.

In FIG. 9 is shown a device 1 wherein the removable connecting means 32 are of the bayonet type. In this case the prosthesis 2 comprises at its base 2a a flange 55 conveniently shaped to be coupled at a corresponding flange 56 placed around the opening 39 of the underpants 31. On the flanges are arranged two holes, respectively, for said duct 17 and said duct 17' of said first inflating means 15.

At last, according to a further embodiment of the invention, the prosthesis 2 may be combined with a prophylactic in such a way to guarantee also the protection against possible sexually transferable diseases.

The invention claimed is:

1. Device for fulfilling a sex act, comprising a tubular shaped prosthesis that extends for a partial length of a male member and is placed, at least partially, around the male member, at the base thereof, and means for retaining in place said prosthesis around the male member, said retaining means comprising a harness placeable around the user's waist, wherein said harness being underpants and in that said prosthesis is inflatable and comprises a first outer surface of an elastic material, and a second inner surface of an elastic material, placed facing the surface of said male member.

2. Device according to claim 1, wherein said prosthesis is essentially C-shaped.

3. Device according to claim 2, further comprising an elastic strip to limit the opening of said C-shaped prosthesis when it is placed around said member.

4. Device according to claim 1, wherein a plurality of stiffening radial diaphragms are disposed between said first and said second surfaces.

5. Device according to claim 1, wherein said prosthesis comprises an elastic pad, inflatable and constrained to said prosthesis at said second inner surface.

6. Device according to claim 1, further comprising first means to inflate said prosthesis.

7. Device according to claim 4, wherein said first inflating means are adaptable for said elastic pad as well.

8. Device according to, claim 1, wherein said prosthesis is integral with said retaining means.

9. Device according to claim 1, wherein said retaining means comprise an opening placed at said member base and a pocket disposed around said opening and accommodating said prosthesis.

10. Device according to claim 1, wherein said prosthesis is connected to said retaining means by removable connecting means.

11. Device according to claim 10, wherein said connecting means comprise bayonet connecting means, or male/female connecting means, or interference connecting means, or VELCRO® connecting means, or adhesion connecting means.

12. Device according to claim 10, wherein said removable connecting means comprise a plurality of folding portions placed at said opening and connectable by adhesion to said prosthesis.

13. Device according to, claim 1, wherein said prosthesis is provided with means to release a wetting substance.

14. Device according to claim 13, wherein said releasing means comprise depressed portions along the outer surface of said prosthesis, said depressed portions being disposed to contain said wetting substance.

* * * * *